United States Patent [19]

Gustafsson

[11] Patent Number: 4,473,421

[45] Date of Patent: Sep. 25, 1984

[54] PROCEDURE FOR MANUFACTURE OF A PROSTHESIS

[75] Inventor: Bengt Gustafsson, Anderstorp, Sweden

[73] Assignee: Otto Bock Scandinavia AB, Norrkoping, Sweden

[21] Appl. No.: 372,146

[22] Filed: Apr. 27, 1982

[30] Foreign Application Priority Data

May 14, 1981 [SE] Sweden .............................. 8103030

[51] Int. Cl.³ ....................... B29C 17/04; A61F 3/00; B28B 3/06
[52] U.S. Cl. .................................. 156/214; 264/296; 264/DIG. 30; 3/4; D24/64
[58] Field of Search .......................... 3/2, 4, 19, 22, 6; 128/89 R, 90, 80 R; 264/222, DIG. 30, 320, 322, 345, 296, 102, 331.12, 571; 156/102, 103, 212, 214, 228, 245, 273, 215; D24/64

[56] References Cited

U.S. PATENT DOCUMENTS

| | | | |
|---|---|---|---|
| 1,099,938 | 6/1914 | Rowley | 3/19 |
| 2,671,225 | 3/1954 | Schoene et al. | 3/19 |
| 3,377,416 | 4/1968 | Kandel | 3/19 |
| 3,393,407 | 7/1968 | Kandel | 3/20 |
| 3,889,301 | 6/1975 | Bonner, Sr. | 3/21 |
| 3,962,395 | 6/1976 | Hägglund | 264/222 |

*Primary Examiner*—Edward C. Kimlin
*Assistant Examiner*—Louis Falasco

[57] ABSTRACT

Procedure for the manufacture of an artificial leg with a sleeve for the fixing of the artificial limb to the remaining part of the leg, in which the procedure embraces the manufacture of a positive model of the extremity which is used for forming the sleeve which is built into the artificial limb.

The purpose of the invention is to facilitate individual adaptation concerning the form of the sleeve so that total surface contact is achieved against the leg, and also to reduce the manual work and the risk of failure.

The invention is characterized by the sleeve being manufactured from an injection moulded standard sleeve of clear thermoplastic material with truncated conic form which forms an inner sleeve in the finished sleeve. The inner sleeve is roughly shaped after the model in heated condition and is tried on the leg, when any deviations in form and irregularities in contact pressure are established by visual inspection through the clear material of the inner sleeve, after which the shape is finally adjusted in one or more steps. When essentially total surface contact has been achieved the inner sleeve is strengthened externally by laminating and is built into the artificial limb.

7 Claims, No Drawings

PROCEDURE FOR MANUFACTURE OF A PROSTHESIS

BACKGROUND OF THE INVENTION

The present invention concerns a procedure for the manufacture of a prosthesis for an extremity, principally an artificial leg of the kind that has for its attachment a sleeve which encloses the end of the remaining part of the extremity.

In the manufacture of prostheses, principally artificial legs, a positive model of that part of the extremity that remains, and which is to serve for the attachment of the artificial leg itself, is produced. In the normal course of events this model is made of a material like plaster, for example. Starting from this positive model a sleeve is then formed from a piece of thick sheet thermoplastic material which shall have as good contact as possible with the extremity. In practice, the formation of this sleeve is done in such a way that the sheet of material, which can have a thickness of about 25 mm, is heated in an oven until it becomes plastic, after which it is formed around the model, preferably by hand. This is an extremely laborious job which both takes a long time and also runs the risk of failure, among other things because the wall thickness of the finished sleeve will vary to a degree that cannot be accepted on account of the large deformations that are necessary, and furthermore in certain cases runs the risk of being so small that holes or perforations in or at the end of the sleeve can easily appear. If such a situation arises the work must be recommenced, since the sleeve cannot be repaired. In addition the forming of the heated plastic material over the model in this manner means that the surface structure of the plastic material, which in the beginning was smooth, will be damaged, for which reason it is impossible to manufacture a sleeve which is transparent over the whole or the major part of its surface even if a perfectly clear plastic material should be used.

When the sleeve has been completed in this manner, the furthermost end is provided with a check valve so that air can be released from the sleeve but not into it, and by this means the sleeve is firmly attached by suction to the end of the amputated extremity. Furthermore, using all available means, the shape of the sleeve must be checked in such a way, and if necessary so adjusted, that total contact exists if possible between the inside of the sleeve and the end of the amputated extremity. In addition the sleeve must be adapted to the shape of the extremity so that the surface pressure on the extremity will if possible be uniform.

This individual fitting of the sleeve is extremely troublesome since the patient has a very bad idea of where the pressure is too great, or where there is no surface contact at all. From this it follows that this individual fitting is very time-consuming and that there exists no guarantee that the result will be good.

It is also possible, and occurs in certain cases, that X-ray is used in the individual fitting of the sleeve. This method is however expensive and also to a certain extent time-consuming, and furthermore it can also be debatable for the reason that radiation doses that are repeated too often and of too high an intensity can be injurious.

When the sleeve has been adapted to the shape of the amputated extremity as well as it can be done the sleeve is subsequently built into the artificial limb itself and serves as its attachment to the extremity and its maneuvering. In a practical case, when an artifical leg is concerned, the sleeve can therefore have a diameter at the further end of magnitude 10–15 cm, while the diameter at the nearer end can be somewhat larger, and the length of magnitude 40 cm.

As has been indicated above, the familiar technique has quite a number of disadvantages. First of all, the essentially manual manufacture of the sleeve means both a high consumption of time and a great risk of failure or at any rate a less good result, depending amongh other things upon irregularities in the wall thickness of the sleeve, or in damage to the surface structure of the sleeve, or even upon the formation of creases in the sleeve material. Furthermore, the methods that are used for the individual fitting of the sleeve are quite inadequate since they are time-consuming and do not lead to a sure result.

SUMMARY OF THE INVENTION

The purpose of the present invention is therefore to achieve a procedure for the production of an artifical limb which eliminates the above-mentioned disadvantages in the familiar technique, and which perhaps above all makes it possible to check and adjust the shape of the sleeve with a very high degree of certainty when it is individually fitted so that a substantially complete surface contact with uniform surface pressure is achieved over the whole of the interior surface of the sleeve against the corresponding part of the extremity.

This objective is achieved in accordance with the invention by means of a procedure which includes a stage in which a positive model of an end section of the remaining extremity is produced, and that from this model is produced a sleeve, closed at one end, which is built into the artificial limb, which procedure is characterized by the fact that the sleeve is produced initially from a prefabricated inner sleeve made of a clear material, preferably acrylic plastic, which is shaped after the model, that the shaped inner sleeve is placed upon the extremity, and departures, if any, in form or irregularities in contact pressure between the extremity and the internal surface of the inner sleeve are established by visual inspection through the material of the inner sleeve, and that the shape of the inner sleeve is matched to the extremity in one or more steps until essentially total surface contact with uniform pressure has been achieved, and that the inner sleeve is subsequently strengthened externally until the necessary strength has been acquired.

In order to make the manufacturing process more rational, but also in order to give a better quality to the final result, it is advisable according to the invention for the inner sleeve, preferably through the injection moulding of a transparant material, to be given the form of a truncated cone with the smaller end closed, in which both the inner and the outer surface of the inner sleeve are made smooth for good transparency through the wall of the inner sleeve.

In order to protect the surface structure of the inner sleeve against damage as far as possible, but also in order to form the inner sleeve as accurately as possible after the plaster model, it is advisable according to the invention for the inner sleeve to be heated until it is deformable and then placed over the model, for the inner sleeve to be sealed against the model along its opening, and for the air between the model and the inner sleeve to be sucked out and the inner sleeve formed after the model.

In order to ensure that the basic shape of the inner sleeve is not lost in connection with individual adaptation, it is advisable according to the invention for the form adaptation of the inner sleeve to the extremity to be carried out by a preferably local heating of the inner sleeve.

The invention will now be described in detail using a concrete operative example that is not of a limiting but only exemplifying nature.

DETAILED DESCRIPTION OF THE PREFERRED EMBODIMENTS

According to the invention one or more sizes of a standard sleeve are mass-produced, preferably by injection moulding, which will form an inner sleeve to that sleeve which constitutes the attachment of the artificial limb to the remaining part of the extremity. This inner sleeve must be of such a strength that it can be adapted while retaining a form which as closely as possible agrees with the external form of the remaining extremity. In a practical example, concerning an aritifical leg, this standard sleeve can have the form of a truncated cone with the smaller end closed, i.e. the further end, and which there has a diameter of magnitude 110 mm. The diameter at the open larger end, i.e. the nearer end, is suitably of magnitude 220 mm. The length of the sleeve is about 450 mm, while the wall thickness can vary between 2 and 5 mm, preferably 3.5–4 mm. Naturally more than one such standard sleeve can be manufactured, for example for artificial limbs intended for children, and it is also possible to produce complete series of such standard sleeves, so that the deformations that the sleeve must undergo during formation after the plaster model will be as small as possible.

In the production of such standard sleeves a thermoplastic material is used, which even after injection moulding retain these properties whereby heating of the sleeve to a relatively low temperature will make the sleeve deformable in a permanent way. In practice, acrylic plastic is often suitable, partly because acrylic plastic has suitable thermoplastic properties, partly because acrylic plastic is not perceived to be a skin irritant or the like.

In the production of the standard sleeve it is essential that both the internal and the external surface of the sleeve material are made completely smooth so that the sleeve is perceived as a clear and completely transparent body, through which in other words an internal object placed in the sleeve can be observed through the material of the sleeve without being obscured or too severely distorted by irregularities in the surface structure of the material of the sleeve or in sudden variations in the wall thickness of the material of the sleeve. These requirements do not however collide with certain desiderata which can sometimes arise, that the bottom of the sleeve, i.e. the further end, in its finished state is to have a somewhat greater wall thickness than is the case for the remainder of the sleeve. For this reason, and even for other reasons, the transition between the bottom of the sleeve and the casing is made gently curved. In order to achieve this distribution of thickness in the finished state it can however be suitable to manufacture the standard sleeve with a wall thickness of about 3.5 mm at the further end and then let the thickness increase continuously to about 4 mm at the nearer end. The reason for this reversed distribution of thickness is that the standard sleeve stretches most at the nearer end when shaping over the plaster model, and therefore the wall thickness decreases most there.

In order to adapt a standard sleeve produced as above (possibly one chosen from a whole series of standard sleeves) so that it receives a shape which as nearly as possible coincides with the shape of the remaining stump of the extremity, a positive model of the extremity is used in a way which in itself is conventional. Such a positive model is as a rule made of plaster, which is cast in a negative model, which in turn is produced directly on the extremity. In accordance with the invention the positive model is formed with a collar or base at the larger end. In the base a lead-in is arranged through which an air tube can be passed that ends at the surface of the model itself. In accordance with the invention it is also essential that the model is given as smooth a surface structure as possible in order that the surface structure of the model shall not influence the surface structure of the sleeve when this is formed after the model and thereby cause the transparency of the sleeve to be imparied or even to be completely lost.

In order that the prefabricated standard sleeve can be formed after the model, the standard sleeve, i.e. the sleeve that will form an inner sleeve of the fastening sleeve of the extremity, is heated in an oven so that the material of the inner sleeve can be deformed. Here the sprue stalk of the inner sleeve can conveniently be left behind in the manufacture and can be used for the suspension of the inner sleeve, since the sprue stalk is as a rule placed in the centre of the farther end of the sleeve. When the inner sleeve has acquired the proper temperature, often about 185° C., it is placed over the model, which it is also advisable to preheat, after which a peripheral region at the open end of the sleeve is tightened to sealing contact around the base of the model, and the air between the model and the sleeve is slowly sucked out, so that the sleeve under the influence of the external air pressure is formed to accurate contact against the model. It is important in this connection that the standard sleeve from the very beginning has such a shape and such dimensions that the required deformation is made as small as possible. Futhermore, through the deformation method of the inner sleeve described, the advantage is realized that no involvement with tools or hands is required on the material of the sleeve, whereby the surface structure does not run the risk of being damaged. Since the model has also been given a relatively smooth surface structure, no damage to the material of the sleeve or to its surface structure will occur either on the inside of the inner sleeve, which would easily be the case if the sleeve was formed by hand, starting from a sheet of material, such tools are often used in such manufacturing processes that can easily give large local compression forces. Since also the deformation of the prefabricated standard sleeve is restricted to a relatively insignificant adaptation of its form, the risk of creasing and other irregularities in the material is eliminated.

After the sleeve has been formed in this way after the model, which can also be preheated in order to facilitate the forming process, the sleeve, and where applicable the model, are permitted to cool so that the sleeve retains the intended shape. The model is then removed from the sleeve and the latter is trimmed along its edges.

The inner sleeve produced in this way has by and large a perfect fit to the plaster model, but despite this it must in most cases be individually fitted to the extremity that it is intended to enclose. In accordance with the invention this is done in such a way that the trimmed and preliminarily formed inner sleeve is placed on the extremity, after which the air is sucked out between the extremity and the sleeve, so that a pressure force is created from the sleeve toward the skin. Since the sleeve produced in accordance with the invention is quite translucent and completely transparent over essentially the whole of its surface, it is possible to check visually the contact between the inner surface of the sleeve and the extremity. This visual inspection is based upon the fact that the skin very soon changes colour in places where the pressure is too high (the skin becomes white). Furthermore it is also easy to localize through the material of the sleeve such parts that may not have satisfactory contact between the skin and the inner surface of the sleeve. In accordance with the invention the discrepancies in the form of the sleeve discovered in this manner are corrected by heating the sleeve, preferably locally, after which its shape is adapted and a new inspection is made. The procedure is repeated until an essentially complete surface contact with uniform surface pressure has been established over the whole inner surface of the sleeve, in other words including the bottom surface of the sleeve which lies against the very end of the remaining part of the extremity.

As has been mentioned before, the inner sleeve has a comparatively small wall thickness, often of magnitude 2-5 mm. This means that the sleeve only has a limited strength that is insufficient for the sleeve to be able to form the holder of the artificial limb at the extremity. For this reason the inner sleeve must be strengthened and its wall thickness increased by a further 2-5 mm, typically 3 mm. In practice this is carried out in such a way that the finished inner sleeve is filled with a plaster mix that is allowed to set in the sleeve, and in this way this cannot be deformed during working operations. Subsequently a laminate is built up on the outside of the sleeve of suitable fibrous material, for example fibre glass, carbon fibre, synthetic fibre, or other suitable fibres, and a plastic composition which can combine with the fibre, and which can combine with, or adhere properly to, the outside of the sleeve. By this building up of the sleeve with two different components, the inner formed component and the outer formed laminate, it is possible at the same time to retain a very good form exactness for the whole sleeve and to give it a wall thickness which varies in a proper manner with regard to strength.

After the sleeve has been built up with a laminate to a suitable thickness and form, and it has completely dried and hardened so that the sleeve has thereby acquired the intended strength and wall thickness, the plaster fill is removed from the inner sleeve which is then cleaned. The sleeve can then be considered ready for fixing to the artificial limb itself, which can be carried out in a conventional manner.

I claim:

1. A procedure for manufacturing a prosthesis for an extremity remainder, said prosthesis having a substantially rigid sleeve defining internal and external surfaces and contacting, with substantially all said internal surfaces said extremity remainder, said procedure includes stages wherein a positive model of an end part of said extremity remainder is made and a sleeve, closed at one end, is manufactured from said model by vacuum forming a prefabricated standard sleeve, in heated condition, on said model and building the sleeve thus formed into said prosthesis, characterized by the standard sleeve manufactured initially from a transparent material and given a surface structure so as to obtain transparency through said material of said standard sleeve and preserve said transparency during the forming of said standard sleeve on said model, said sleeve so formed is placed on said extremity remainder and any deviation in form and irregularities in contact pressure between said extremity remainder and said internal surface of said formed sleeve is established by visual inspection through said transparent material, the formed sleeve fitted to said extremity remainder until substantially total surface contact with uniform pressure is established between said internal surface and said extremity remainder and said formed sleeve is thereafter strengthened externally.

2. A procedure in accordance with claim 1, characterized by the standard sleeve, preferably by injection molding of a transparent acrylic plastic, being given the form of a truncated cone defining a closed small end and an outer surface with both the internal and external surfaces of the standard sleeve made smooth for good transparency through the cone of the standard sleeve.

3. A procedure in accordance with claim 1 or 2, characterized by said formed sleeve being fitted to said extremity remainder by local heating of said formed sleeve.

4. A procedure in accordance with claim 3, characterized by the substantially rigid sleeve being heated to deformability and placed over the model and sealed against the model opposite said closed small end, said sleeve formed on said model by removal of any air between said model and said sleeve.

5. A procedure for manufacturing a prosthesis for an extremity remainder, said prosthesis having a substantially rigid sleeve defining internal and external surfaces and contacting, with substantially all said internal surface, said extremity remainder;

said procedure includes stages wherein a positive model of an end part of said extremity remainder is made and a sleeve, closed at one end, is manufactured from said model by vacuum forming a prefabricated standard sleeve, in heated condition, on said model and building the sleeve thus formed into said prosthesis, characterized by the standard sleeve manufactured initially from a transparent material and given a surface structure so as to obtain transparency through said material of said standard sleeve and preserve said transparency during the forming of said standard sleeve on said model;

said sleeve so formed is placed on said extremity remainder and any deviation in form and irregularities in contact pressure between said extremity remainder and said internal surface of said formed sleeve is established by visual inspection through said transparent material;

the formed sleeve fitted to said extremity remainder by heating said formed sleeve, preferably locally, and manually shaping said formed sleeve until essentially total surface contact with uniform pressure is established between said formed sleeve and said extremity remainder and said formed sleeve is thereafter strengthened externally by application of a plastic laminate.

6. A procedure according to claim 5, characterized by the standard sleeve, preferably by injection molding of a transparent acrylic plastic, being given the form of a truncated cone defining a closed small end and an outer surface with both the internal and external surface of the standard sleeve made smooth for good transparency through the cone of the standard sleeve.

7. A procedure in accordance with claim 6, characterized by the substantially rigid sleeve being heated to deformability and placed over the model and sealed against the model opposite said closed small end, said sleeve formed on said model by removal of any air between said model and said sleeve.

* * * * *